United States Patent
Cleris et al.

(10) Patent No.: US 7,338,203 B2
(45) Date of Patent: Mar. 4, 2008

(54) METHOD FOR DETERMINING VANISHING TEMPERATURE OF PETROLEUM PRODUCT CRYSTALS AND DEVICE THEREFOR

(75) Inventors: Hervé Cleris, Curcy sur Orne (FR); Olivier Lara, Jaunay-Clan (FR)

(73) Assignee: I.S.L., Verson (FR)

( * ) Notice: Subject to any disclaimer, the term of this patent is extended or adjusted under 35 U.S.C. 154(b) by 2 days.

(21) Appl. No.: 10/531,502

(22) PCT Filed: Oct. 29, 2003

(86) PCT No.: PCT/FR03/03222

§ 371 (c)(1), (2), (4) Date: Oct. 5, 2005

(87) PCT Pub. No.: WO2004/042385

PCT Pub. Date: May 21, 2004

(65) Prior Publication Data

US 2006/0098708 A1    May 11, 2006

(30) Foreign Application Priority Data

Oct. 30, 2002    (FR) .................................. 02 13577

(51) Int. Cl.
*G01N 25/02* (2006.01)

(52) U.S. Cl. .......................................... 374/16; 374/17

(58) Field of Classification Search .................. 374/16, 374/17

See application file for complete search history.

(56) References Cited

U.S. PATENT DOCUMENTS

| 3,457,772 A | 7/1969 | Chassagne et al. |
| 4,519,717 A | 5/1985 | Jones et al. |
| 4,572,676 A * | 2/1986 | Biermans et al. ............. 374/17 |

FOREIGN PATENT DOCUMENTS

| DE | 100 56 131 A | 5/2001 |
| EP | 0 328 334 A | 11/1994 |

* cited by examiner

*Primary Examiner*—Gail Verbitsky
*Assistant Examiner*—Megann E Vaughn
(74) *Attorney, Agent, or Firm*—Baker & Daniels LLP

(57) ABSTRACT

The invention concerns a method for determining the vanishing temperature of petroleum product crystals, characterized in that it comprises the following steps: introducing the sample to be analyzed in a measuring cell (4), arranged in a cryostatic chamber (1); connecting a laser emitter (6) and an associated optical receiver (7) to pass an optical beam through the sample to be analyzed and recording the light intensity received by the receiver (7); gradually lowering the temperature of the cryostatic chamber (1) then increasing it again gradually while recording the curve representing the variations in the light intensity received by the receiver (7) based on the temperature; and determining the vanishing temperature of the crystals from said curve.

12 Claims, 4 Drawing Sheets

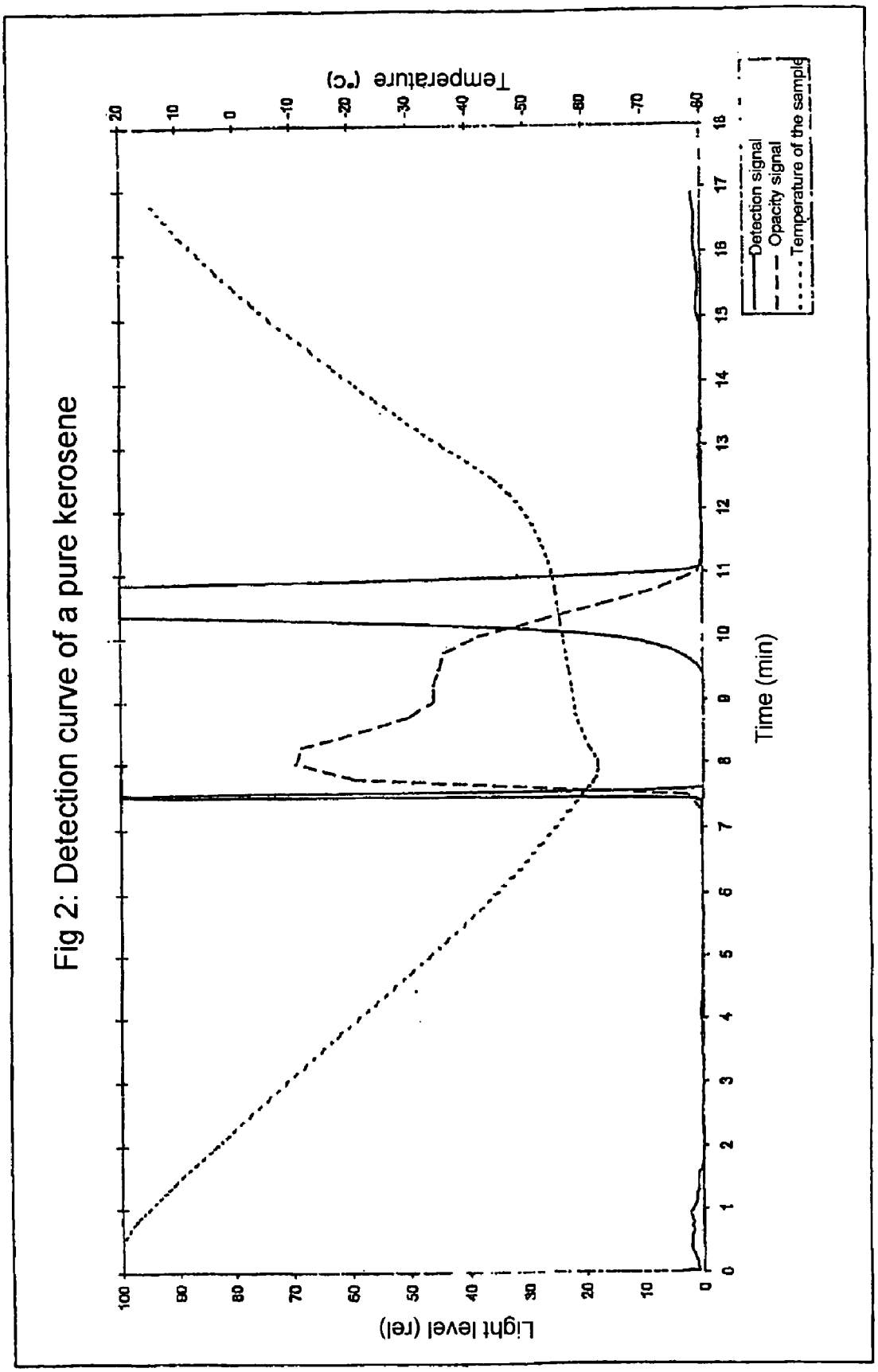

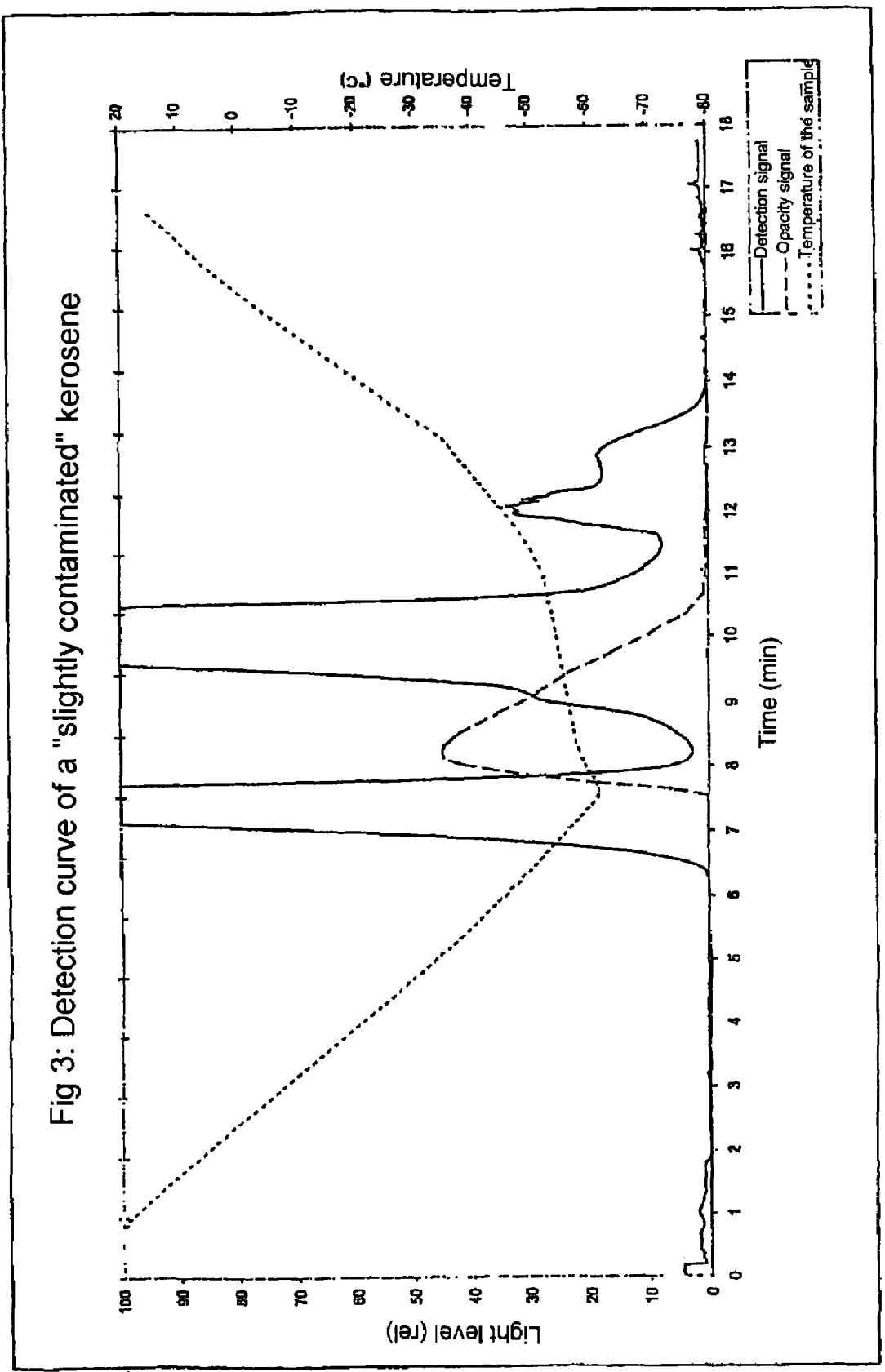

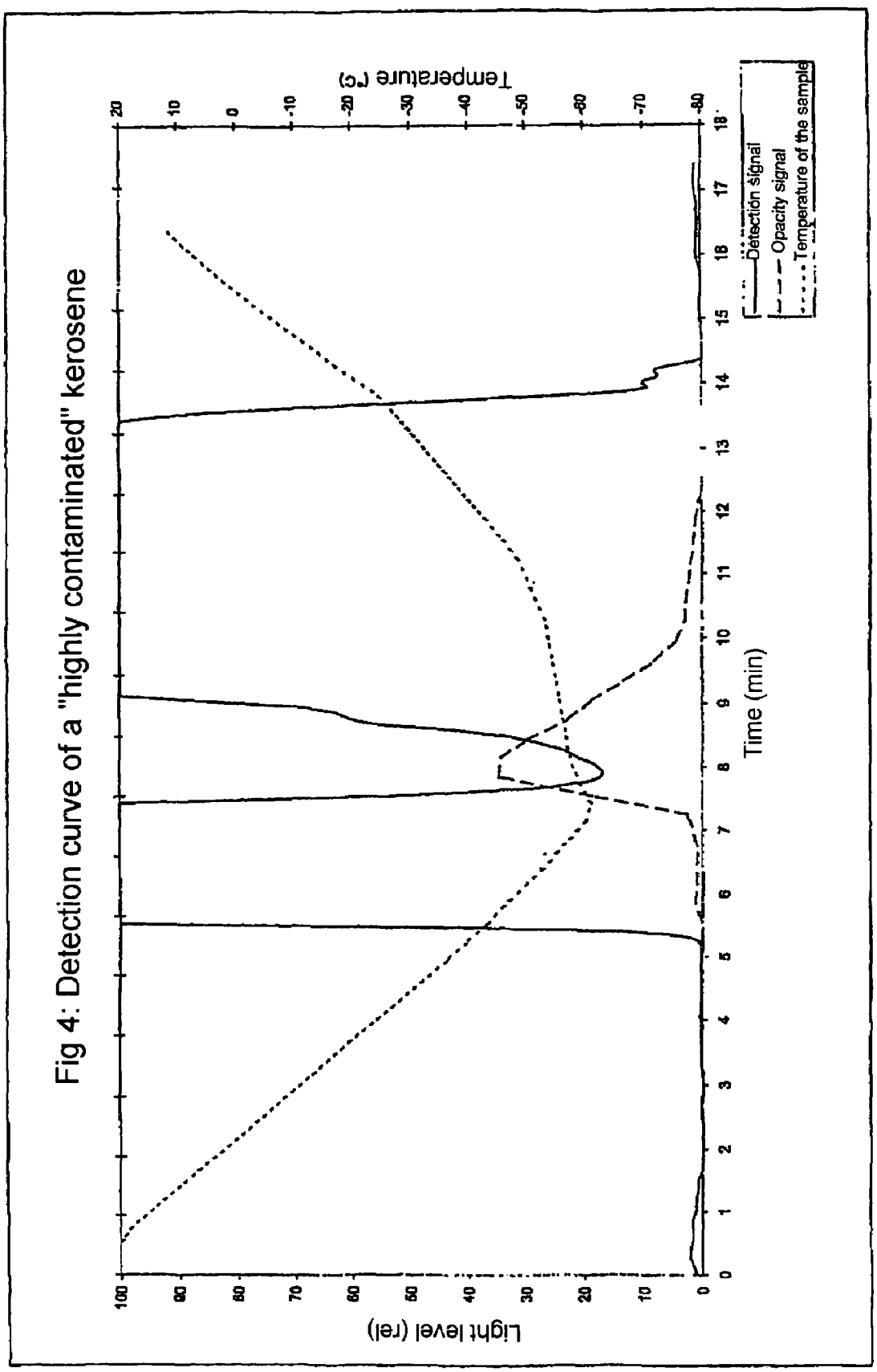

METHOD FOR DETERMINING VANISHING TEMPERATURE OF PETROLEUM PRODUCT CRYSTALS AND DEVICE THEREFOR

The present invention relates to a method of determining the vanishing point of petroleum product crystals, especially crystals of kerosenes intended for aviation in a temperature range of approximately from −5° C. to −120° C.

The vanishing point of crystals is defined as the temperature at which the last crystals in a previously crystallised sample vanish, in the course of a gradual rise in temperature.

There are various standards that define the conditions for obtaining the vanishing point of crystals; this is of particular interest to specialists in the field of aviation, since it permits determination of the time for which an aircraft may remain at a given high altitude without the risk of the fuel transfer pipes and the filters becoming blocked.

Moreover, the value of the vanishing point of crystals indicates whether a kerosene is pure or is contaminated with gas oil.

Various apparatuses permitting the determination of the vanishing point of the crystals of petroleum product samples are currently available on the market.

Among those apparatuses there may be mentioned by way of example the apparatuses marketed by ISL under the names FZP 5 Gs and FZP 5 G, which are fully automated apparatuses which operate with implementation of standards ASTM D 2386, IP 468 and ISO 3013.

The principle of such apparatuses consists, schematically, in passing a light beam emitted by a diode through a measuring cell containing the sample to be tested, which cell is located in a cryostatic chamber equipped with a temperature sensor connected to cooling and temperature control members, and in detecting the light intensity received by an optical receiver aligned with the infra-red emitter through the measuring cell containing the samples to be analysed.

In order to carry out this test, the temperature of the cryostatic chamber is gradually lowered until the optical detector no longer receives any light, which means that the sample has crystallised completely, then the temperature is gradually raised again while the curve representing the variations in the light intensity received by the optical receiver as a function of the temperature is recorded.

When the last crystals have vanished from the sample, a break is observed in the curve, which corresponds to the vanishing point of the crystals, followed by a level section.

Such an apparatus has the advantage of being compact and automatic, therefore being capable of giving perfectly reproducible results without being dependent on the skill of an operator.

However, it has the disadvantage that its sensitivity may prove inadequate in some cases, especially when it is desired to determine the vanishing point of the crystals of a kerosene contaminated with a small proportion of gas oil.

In the presence of gas oil, the vanishing point of the crystals of a kerosene sample increases notably: in the case of a sample containing several % gas oil, the curve showing the variations in the intensity received by the optical detector as a function of the temperature exhibits a sufficiently marked break to determine the vanishing point of the crystals, and consequently the proportion of gas oil, by comparison with the vanishing point of pure kerosene crystals.

In the case of contamination with a smaller proportion, on the other hand, the curve becomes rounded and no longer exhibits a pronounced break, so that it is no longer possible to determine the vanishing point of the crystals.

Another apparatus suitable for determining the vanishing point of crystals is described in U.S. Pat. No. 5,088,833.

The principle of that apparatus, which operates according to standard ASTM D 5972, consists, schematically, in depositing a micro-sample of the product to be analysed in a crucible, the base of which is formed by a mirror cooled by Peltier elements, and gradually cooling the sample until it crystallises before gradually heating it again.

During the test, the sample to be analysed is illuminated by a light beam with an incidence chosen so that the beam reflected on the mirror does not reach an optical detector located opposite the mirror.

When crystals are present in the sample, they diffuse the emitted light in a random manner and part of that light is consequently received by the optical detector.

Consequently, the appearance and disappearance of crystals can be detected by analysing the signal received by the optical detector, which is zero in the absence of crystals and increases as crystals appear in the sample.

That apparatus has the advantage of being sufficiently sensitive to detect a very small amount of gas oil within a kerosene. However, it is not very convenient to use and the results obtained are largely dependent on the skill of the operator.

The object of the present invention is to propose a method of determining the vanishing point of petroleum product crystals, especially crystals of kerosenes intended for aviation, in order to remedy these disadvantages.

According to the invention, this method is characterised by the following steps:

- a laser emitter and an associated longitudinal optical receiver are mounted on either side of a substantially horizontal tubular measuring cell located in a cryostatic chamber equipped with a temperature sensor connected to cooling and temperature control members, so that the optical beam emitted by the laser emitter is aligned with the horizontal axis of the measuring cell and with the longitudinal optical receiver,
- the temperature sensor, the cooling and temperature control members and the longitudinal optical receiver are connected to programmable calculating and display means,
- a diaphragm is mounted directly downstream of the laser emitter so that the optical beam emitted thereby is sufficiently fine to rule out any reflection on the walls of the measuring cell,
- there is mounted, upstream of the longitudinal optical receiver, a polariser which is so adjusted that the optical beam emitted directly by the laser emitter cannot be transmitted,
- the sample to be analysed is introduced into the measuring cell,
- the laser emitter and the associated longitudinal optical receiver are switched on so as to pass an optical beam through the sample to be analysed, and the light intensity received by the longitudinal optical receiver is recorded,
- the temperature of the cryostatic chamber is gradually lowered to the end of crystallisation temperature of the sample to be analysed, or the point of opacity, and then the temperature of the chamber is gradually raised again while the curve showing the variations in the light intensity received by the longitudinal optical receiver as a function of the temperature, or the detection curve, is recorded, and the vanishing point of the crystals is determined from that curve.

This method therefore differs essentially by the use of a polarised light beam, so that the longitudinal optical receiver does not receive any light in the absence of crystals whereas, on the other hand, as soon as crystals appear within the sample to be analysed, a certain amount of light is transmitted to the receiver; it is in fact well known to those skilled in the art that crystals modify the direction of polarisation of light.

Of course, such a method is only possible in the absence of any reflection on the walls of the measuring cell; consequently, the surface condition of the cell is immaterial, but it is imperative that the cross-section of the beam passing through it should be sufficiently reduced by the diaphragm.

According to the invention, it has been established that the diameter of the diaphragm must preferably be of the order of from 1 to 1.5 mm given that, above 1 mm, risks of diffraction may be encountered at that level.

Furthermore, in order to obtain optimum sensitivity of the receiver, the wavelength of the laser beam may advantageously be of the order of 650 nanometres.

According to a preferred feature of the invention, there is also mounted, close to the measuring cell, in the upstream portion thereof, a lateral optical receiver which is connected to the optical beam emitted by the laser emitter and also to the programmable calculating and display means.

The lateral optical receiver does not receive any light in the absence of crystals, given that the sample to be analysed is then perfectly transparent, but receives diffused light as soon as crystals appear in the sample.

During a test, therefore, the curve showing the variations in the light intensity received by the lateral optical receiver as a function of the temperature, or the opacity curve, is likewise recorded, and there is determined, using that curve, the end of crystallisation temperature of the sample to be analysed, or the point of opacity, that is to say the temperature from which the direction of variation of the temperature must be reversed.

Consequently, the function of the lateral optical receiver is to control the method.

More precisely, at the start of the test, the two detectors do not receive any light.

As cooling is carried out, the first crystals appear and modify the polarisation of the light emitted by the laser emitter, and a certain amount of light is thus able to pass through the polariser and reach the longitudinal optical receiver.

When the amount of crystals within the sample to be analysed becomes large, the sample becomes cloudy, thus causing diffusion of the light, part of which reaches the transverse optical receiver.

When the cloudiness becomes very great, the beam emitted by the laser emitter is no longer able to reach the polariser and consequently the light intensity received by the longitudinal optical detector diminishes.

The point of opacity is reached when the light intensity received by the lateral optical receiver increases while the light intensity received by the longitudinal optical receiver diminishes.

When the point of opacity is reached, the temperature of the cryostatic chamber is gradually increased in order to determine the value of the vanishing point of the crystals of the sample on the detection curve.

During this increase, the light intensity received by the longitudinal optical receiver increases from the moment when the sample becomes sufficiently transparent that the beam emitted by the laser emitter is able to reach the polariser, then diminishes again when the last crystals vanish.

The point from which the longitudinal optical receiver no longer receives any light corresponds to the vanishing point of the crystals that is being sought.

The invention relates also to a device permitting implementation of the above-mentioned method.

According to the invention, the device is characterised in that it comprises:

a cryostatic chamber equipped with a temperature sensor connected to cooling and temperature control members, a substantially U-shaped measuring tube which is mounted inside the cryostatic chamber and the central, substantially horizontal, branch of which constitutes the measuring cell while the lateral branches permit the introduction of the sample to be analysed into the cell and its removal, a laser emitter and an associated longitudinal optical receiver, aligned on either side of the measuring cell along the longitudinal axis thereof, a diaphragm mounted directly downstream of the laser emitter, a polariser mounted upstream of the longitudinal optical receiver, and programmable calculating and display means connected to the temperature sensor, to the cooling and temperature control members and to the longitudinal optical receiver.

Taking into account this configuration, the only manual operations to be carried out in order to implement a test consist in introducing the sample to be analysed into the measuring cell by means of a syringe and switching on the laser emitter, the associated longitudinal optical receiver and the cooling and temperature control members.

The test is then carried out automatically under the control of the calculating and display means which have previously been programmed according to the standard to be complied with and which control the cooling and temperature control members according to information transmitted to them by the temperature sensor and at the same time draw up the detection curve according to the information transmitted to them by the longitudinal optical receiver.

According to a preferred feature of the invention, the device comprises a lateral optical receiver mounted close to the measuring cell, in the upstream portion thereof, and connected to the programmable calculating and display means.

According to that feature, the programmable calculating and display means draw up the opacity curve from information transmitted to them by the lateral optical receiver and use that curve to automatically control the cooling and temperature control members and, consequently, the temperature variations inside the cryostatic chamber.

According to the invention, the light intensity is transmitted to the optical receivers by the way of light guides which preferably cooperate with lenses capable of concentrating the optical beam.

Those lenses may advantageously be formed by glass balls having a diameter of from 5 to 8 mm located on the optical axis.

The light guides are in turn preferably composed of fibres located in the focal plane of the lens.

According to another feature of the invention, the measuring tube is constituted by a metal element, especially made of aluminium, provided with ports which permit the passage of the optical beam to be detected.

It is essential that those ports, which are generally of glass, have faces that are perfectly parallel.

According to the invention, the cooling and temperature control members may be constituted by a cooling unit, especially a Stirling cycle cooling unit, the cold finger of which is equipped at its free end with dry contact heat transmission members cooperating with the cryostatic chamber in order to allow it to be cooled to the desired temperature.

A device for analysing petroleum product samples that includes a Stirling cycle cooling unit is described by way of example in document FR-2 801 381.

The use of such a cooling unit corresponds to a particularly advantageous feature of the invention, by virtue of which the device may be constituted by a compact portable apparatus.

The features of the process and device according to the invention will be described in greater detail with reference to the accompanying drawings, in which:

FIGS. 2, 3 and 4 are examples of curves drawn up by the programmable calculating and display means in the case of a sample of pure kerosene, a sample of slightly contaminated kerosene and a sample of highly contaminated kerosene.

Figure 1:
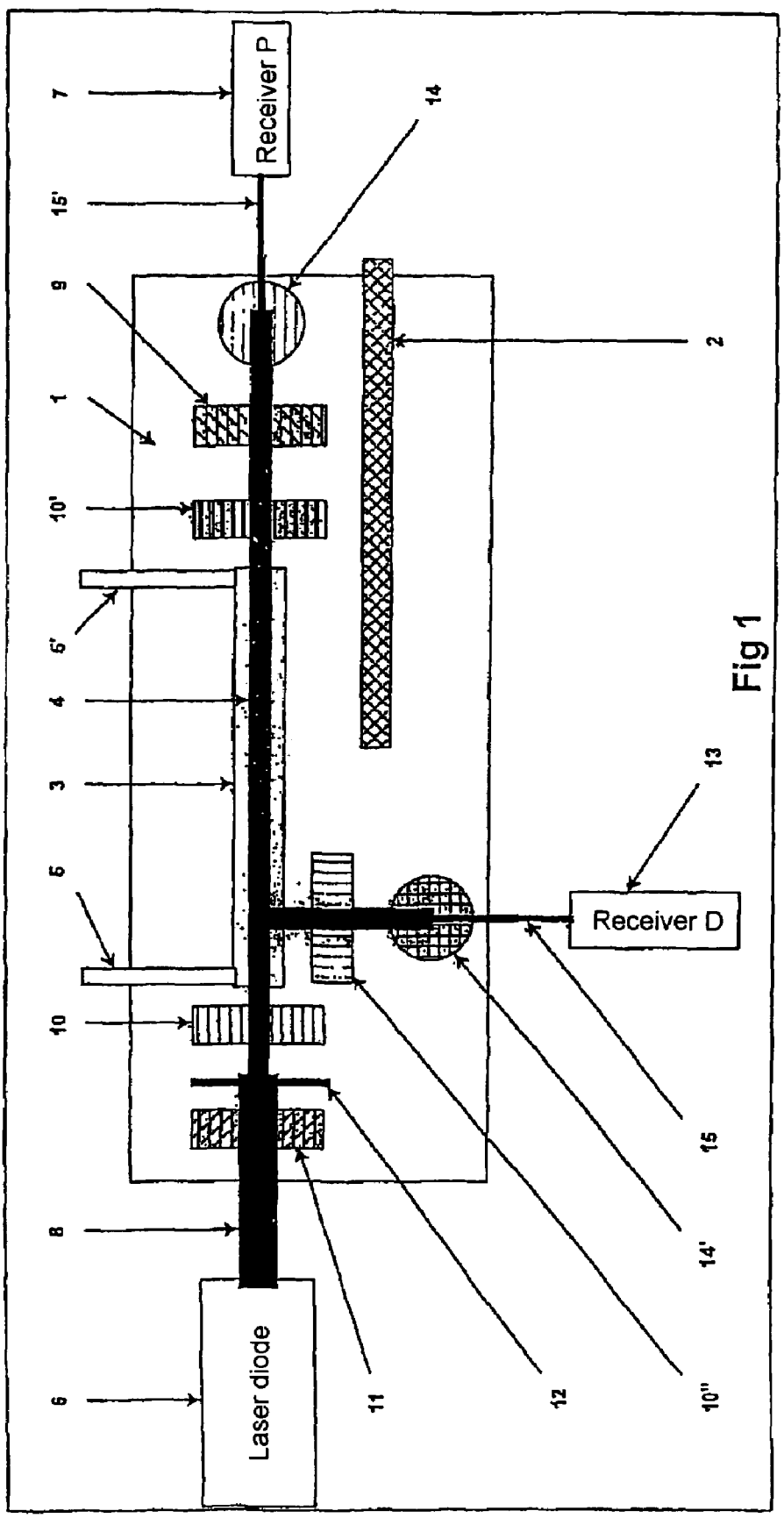
FIG. 1 is a diagram showing the device.

According to FIG. 1, the device corresponds to a compact apparatus comprising a cryostatic chamber 1 equipped with a temperature sensor 2 and a Stirling cycle cooling and temperature control unit (not shown in the Figure) for the chamber 1.

According to FIG. 1, the cryostatic chamber 1 is equipped, on the inside, with a U-shaped metal measuring tube 3, the central horizontal branch 4 of which constitutes the measuring chamber which receives the sample to be analysed.

The lateral branches 5 and 5' of the measuring tube 3 permit the introduction of the sample and its removal.

The apparatus also comprises a laser diode 6 associated with a longitudinal optical receiver 7 so that the emitted laser beam 8 is aligned with the horizontal axis of the measuring cell 4 and passes through the sample to be analysed, which has been introduced into the cell, before reaching the receiver 7.

A polariser 9 is mounted upstream of the longitudinal receiver 7 in the propagation direction of the laser beam emitted by the diode 6.

The polariser 9 is adjusted so that the longitudinal receiver 7 does not receive any light when the sample contained within the measuring cell 4 is transparent and does not contain any crystals.

Glass ports 10, 10' having perfectly parallel faces allow the laser beam 8 to pass through the measuring cell 4 and reach the longitudinal receiver 7, while ensuring that the cell is leak-tight.

An auxiliary polariser 11, crossed with the polariser 9 and mounted directly downstream of the laser diode 6, acts as an amplitude attenuator for the beam emitted by the diode.

The auxiliary polariser 11 cooperates with a diaphragm 12 mounted directly downstream thereof, in order to ensure that the laser beam passing through the measuring cell 4 is sufficiently fine to rule out any reflection on the walls of the cell.

According to FIG. 1, the apparatus also comprises an lateral optical receiver mounted close to the measuring cell 4, in the upstream portion thereof.

A glass port 10" similar to the ports 10 and 10' allows the light diffused at the upstream portion of the measuring cell 34 to reach the lateral receiver 13.

The polarised light leaving the polariser 9 and the diffused light leaving through the port 10" are concentrated on light guides 15, 15' by lenses 14, 14' before reaching the receivers 7, 13.

The cooling unit, the temperature sensor 2 and the longitudinal receiver 7 and the lateral receiver 13 are connected to programmable calculating and display means (not shown) which control the test in accordance with the standard to be complied with.

To that end, the programmable calculating and display means control the cooling unit for the cryostatic chamber 1 in dependence on information transmitted to them by the temperature sensor 2 and by the receivers 7, 13, and draw up, in parallel, the detection curve showing the variations in the light intensity received by the longitudinal receiver 7 and the opacity curve showing the variations in the light intensity received by the lateral receiver 13.

FIGS. 3, 4 and 5 show three examples of such curves corresponding to three different kerosene samples.

More precisely, on the three curves, the time expressed in minutes is plotted on the X-axis, while the light intensity received by the receivers, expressed according to a relative graduation from 0 to 100, and the temperature of the sample expressed in ° C. are plotted on the Y-axis, on the left-hand scale and on the right-hand scale, respectively.

The curves in dotted lines show the variations in the temperature of the sample as a function of time (right-hand scale).

The curves in broken lines correspond to the opacity curves and show the variations, as a function of time, in the light intensity received by the lateral receiver (left-hand scale).

The curves in unbroken lines correspond to the detection curves and show the variations, as a function of time, of the light intensity received by the longitudinal receiver (left-hand scale).

Analysis of those three curves allows the point of opacity to be determined, that is to say the temperature from which the direction of variation of the temperature in the cryostatic chamber must be reversed.

The curves in unbroken lines allow the vanishing point of the crystals to be determined.

According to FIG. 2, in the case of pure, uncontaminated kerosene, the appearance of the first crystals was detected at 7 minutes 30 seconds, that is to say at a temperature of −59° C.

The point of opacity was detected at a temperature very close to −60° C.

The vanishing point of the crystals was detected at 11 minutes, that is to say at a temperature of −54° C.

According to FIG. 3, in the case of a slightly contaminated kerosene, the appearance of the first crystals was detected at 6 minutes 30 seconds, that is to say at a temperature of −45° C., and the point of opacity was detected at 7 minutes 45 seconds, that is to say at a temperature of −60° C.

Disappearance of the cloudiness in the sample was detected at 11 minutes 30 seconds, that is to say at a temperature of −55° C., and the vanishing point of the crystals was detected at 13 minutes 30 seconds, that is to say at a temperature of −38.7° C.

The "rebound" noted on the detection curve at about 12 minutes does not seem to be associated with the material used but rather with physical phenomena within the sample.

According to FIG. 4, in the case of a highly contaminated kerosene, the vanishing point of the crystals was detected at 14 minutes 30 seconds, that is to say at a temperature of −27.5° C.

The invention claimed is:

1. A method of analyzing a sample, comprising the steps of:
   providing an apparatus, comprising:
      a laser emitter and an associated longitudinal optical receiver mounted on either side of a horizontal tubular measuring cell located in a cryostatic chamber equipped with a temperature sensor connected to cooling and temperature control members, so that an optical beam emitted by the laser emitter is aligned with a longitudinal axis of the measuring cell and with the longitudinal optical receiver, and wherein the temperature sensor, the cooling and temperature control members and the longitudinal optical receiver are connected to programmable calculating and display means;
      a diaphragm mounted directly downstream of the laser emitter, the diaphragm reducing a cross section of the optical beam to prevent reflection of the optical beam on the walls of the measuring cell;
      a polarizer mounted upstream of the longitudinal receiver, the polarizer oriented such that the optical beam initially emitted by the laser emitter cannot be transmitted therethrough; and
      a lateral optical receiver mounted proximate to an upstream portion of the measuring cell, the lateral optical receiver connected to the programmable calculating and display means and receiving the optical beam emitted by the laser emitter;
   obtaining a sample;
   introducing the sample into the measuring cell;
   activating the laser emitter, the longitudinal optical receiver and the lateral optical receiver to pass an optical beam through the sample;
   gradually lowering the temperature of the cryostatic chamber while recording a detection curve showing the variations in light intensity received by the longitudinal optical receiver as a function of the temperature, and an opacity curve showing the variations in the light intensity received by the lateral optical receiver as a function of the temperature;
   determining, using the opacity curve, at least one of the end of crystallization temperature and the point of opacity of the sample;
   gradually raising the temperature of the chamber while continuing to record the detection curve and the opacity curve; and
   determining the vanishing point of crystals in the sample from the detection curve within a temperature range of −5 to −120° C.

2. The method of claim 1, wherein the apparatus further comprises a substantially U-shaped measuring tube mounted inside the cryostatic chamber and having a central, substantially horizontal branch constituting the measuring cell and lateral branches through which the sample is introduced into the cell and is removed from the cell, respectively.

3. The method of claim 1, wherein the light intensity is transmitted to the longitudinal and lateral optical receivers by light guides.

4. The method of claim 3, wherein the light guides cooperate with lenses capable of concentrating the optical beam.

5. The method of claim 1, wherein the apparatus further comprises a measuring tube formed as metal element and including ports permitting the passage of the optical beam.

6. The method of claim 1, wherein the cooling and temperature control members are constituted by a cooling unit having a cold finger equipped with dry contact heat transmission members cooperating with the cryostatic chamber.

7. The method of claim 1, wherein the cooling unit is a compact portable device.

8. The method of claim 1, wherein the sample is a petroleum product.

9. The method of claim 8, wherein the petroleum product is aviation kerosene.

10. The method of claim 1, further comprising the step of determining whether the petroleum product is pure or polluted based on the vanishing point of crystals.

11. The method of claim 1, wherein the apparatus further comprises an auxiliary polarizer mounted downstream of the laser emitter and upstream of the measuring cell, the auxiliary polarizer oriented perpendicularly to the polarizer.

12. The method of claim 1, wherein the diaphragm includes an aperture having a diameter between 1 mm and 1.5 mm.

* * * * *